United States Patent [19]

Hässig

[11] Patent Number: 4,676,982

[45] Date of Patent: Jun. 30, 1987

[54] TREATMENT OF CHRONIC INFLAMMATORY DISEASE WITH POLYVALENT IMMUNOGLOBULINS

[75] Inventor: Alfred Hässig, Stettlen, Switzerland

[73] Assignee: Central Laboratory of the Swiss Red Cross Blood Transfusion Service, Berne, Switzerland

[21] Appl. No.: 892,655

[22] Filed: Aug. 4, 1986

[30] Foreign Application Priority Data

Aug. 7, 1985 [GB] United Kingdom ............... 8519848

[51] Int. Cl.⁴ ............................................ A61K 39/395
[52] U.S. Cl. ........................................ 424/85; 530/387
[58] Field of Search ......................... 424/85; 530/387

[56] References Cited

U.S. PATENT DOCUMENTS 4,617,266 10/1986 Fahnestock ........................ 435/68

OTHER PUBLICATIONS

Acta Path. Microbiol. Scandinav. 75, 466–480 (1969), Forsgren et al.
Journal of Immunology, 103, 467–473 (1969), Sjoquist et al.
Journal of Immunology, 97, 822–827 (1966), Forsgren et al.
Acta Path. Microbiol. Scandinav. 73, 400–406, (1968), Grov.

*Primary Examiner*—Howard E. Schain
*Attorney, Agent, or Firm*—Gerald D. Sharkin; Robert S. Honor; Thomas O. McGovern

[57] ABSTRACT

Chronic inflammatory disease of the bowel, e.g. ulcerative colitis and Crohn's disease, is treated by infusion of an intravenously injectable form of a polyvalent, intact immunoglobulin (IgG).

6 Claims, No Drawings

TREATMENT OF CHRONIC INFLAMMATORY DISEASE WITH POLYVALENT IMMUNOGLOBULINS

The present invention relates to a novel method for the treatment of chronic inflammatory disease, particularly chronic inflammation of the bowel.

Certain inflammatory conditions of the bowel are of unknown etiology and are difficult to treat. One such disease is ulcerative colitis; a severe inflammation and ulceration of the mucosa and submucosa of the large intestine. Another is Crohn's disease, in which a similar condition affects the ileum. In both cases the intestinal mucosa become swollen, painful and liable to bleed easily, giving rise to symptoms of abdominal cramps, frequent need to defecate and bloody mucous stools.

Treatment is generally by medication with drugs such as sulfasalazine and cortiosteroids. These generally give some relief, but do not cure the chronic condition. In severe cases surgical removal or bypass of the affected portion of intestine may be necessary.

It has now been found that chronic inflammatory diseases of this type, particularly ulcerative colitis and Crohn's disease, may be successfully treated by intravenous administration of immunoglobulin. Accordingly, the present invention provides a method of treating chronic inflammatory disease of the bowel, which method comprises intravenous administration of an effective amount of an intravenously injectable form of a polyvalent, intact immunoglobulin (IgG).

By a polyvalent, intact IgG is meant one which has not been cleaved (for example with high pepsin concentrations) and which retains the structural and functional integrity of the 7S-IgG antibodies. Preferably it is one obtained from blood serum fractions by a modified alcohol cryoprecipitation including mild acidification at pH 4. A suitable product is Immunoglobulin SRC produced by the Swiss Red Cross and sold by Sandoz Ltd. under the name Sandoglobulin ®. The in vitro characteristics of this material have been published by J. Römer et al. "Characterization of Various Immunoglobulin Preparations for Intravenous Application. I. Protein Composition and Antibody Content and Characterization of Various Immunoglobulin Preparations for Intravenous Application. II. Complement Activation and Binding to Staphylococcus Protein A." (Vox Sanguinis Vol. 42, No. 2 pp. 62–73 and 74–80), 1982.

The dosage of immunoglobulin to be administered is preferably in the range of 0.05 to 0.3 g/kg of body weight, more preferably 0.1–0.25 g/kg. A typical dosage for an adult is 6–18 g, preferably 12–18 g.

The immunoglobulin is preferably administered by intravenous infusion in the form of a 2–6% solution, more preferably as a 3% solution in sterile physiological saline. A suitable rate of infusion of a 3% solution is, for example, 10 to 20 drops/minute for the first 15 minutes, 20 to 30 drops/minute for a further 15 minutes and 40 to 50 drops/minute thereafter.

The dosage is preferably administered as a single infusion, which may be repeated at intervals of 3 days–4 weeks, preferably 2–4 weeks or as required. No adverse side effects are observed as a result of the treatment.

It is found that in recent cases of ulcerative colitis and Crohn's disease complete and long lasting relief may be obtained after only one or two infusions, but that for patients with a longer history of disease a longer series of infusions may be necessary.

The following Examples illustrate the invention:

EXAMPLE 1

A 28-year old man had been suffering for 2 years from ulcerative colitis, originally with up to 12 passages of bloody stools daily. Treatment with salazopyrin and steroids during this time gave some improvement, but symptoms persisted.

A single infusion of 6 g intravenous IgG (Sandoglobulin ®) was given, followed 6 weeks later by a further infusion of 12 g Sandoglobulin. Ten days after the second infusion the patient felt subjectively better, and had only one defecation daily, with no blood in the stools. Proctoscopic examination showed that the mucosa were still swollen, but no longer exuded blood when the surface was touched. A further examination 3 months later showed the intestinal mucosa practically normal. Medication was discontinued and the patient remained free of symptoms six months after immunoglobulin treatment.

EXAMPLE 2

A 33 year old woman had been treated for ulcerative colitis 6 years previously. The symptoms had never entirely disappeared, and the patient then suffered a new acute attack.

Three infusions each of 12 g Sandoglobulin were given at 2-week intervals. One month after treatment, without concomitant medication, the condition of the patient had improved and abdominal cramps were absent, although defecation was still relatively frequent.

EXAMPLE 3

A 78 year old man had suffered for shortly over 1 year from ulcerative colitis, which did not respond to treatment with salazopyrin and colifoam injection.

Four infusions each of 12 g of Sandoglobulin were given at approximately two-weekly intervals. Two weeks after the final infusion, proctological examination showed a significant decrease in the degree of inflammation.

EXAMPLE 4

A 23 year old man had been diagnosed 6 years earlier as suffering from Crohn's disease, and had been treated intermittently with prednisone. After a year without treatment there was a recurrence of the disease, with stenosis of the terminal ileum, destruction of the normal mucosa and a typical "cobblestone" appearance with deep intermediate fissures. The patient also complained of poor appetite and loss of weight.

A total of 5 infusions of 12 g Sandoglobulin were given at approximately 2-week intervals. At the end of this time, the patient's condition had improved considerably, with no abdominal pain and good appetite. After a further month, psychological stress associated with loss of his job led to a relapse, and the same course of treatment of 5 infusions was repeated, with good results.

EXAMPLE 5

A 31 year old woman suffered from an acute attack of ulcerative colitis following an injury with bruising in the region of the pubic bone. Two years later she suffered a relapse, which at her own wish was treated symptomatically, without use of salazopyrin or steroids. Endoscopic and X-ray examination after a further 3 months showed a state of chronic inflammation extending over the entire large intestine. Investigations for bacterial, amoebic or parasitical infection gave negative results, but blood eosinophile and IgE levels were elevated.

The patient was treated with four infusions each of 12 g Sandoglobulin at 2-week intervals, without concomitant salazopyrin or steroid therapy. Subjective symptoms improved considerably even after the first infusion, and a week after the course of treatment the patient had put on weight, had good appetite and general health, and no longer was subject to frequent attacks of diarrhea.

Ten months later the patient suffered a relapse and was treated with four infusions each of 18 g Sandoglobulin at intervals of 2 weeks to 1 week. Following this treatment the patient was fully recovered and was able to go on a 3-week overseas journey.

What is claimed is:

1. A method of treatment of chronic inflammatory disease of the bowel comprising the intravenous administration of an effective dose of an intravenously injectable form of a polyvalent, intact immunoglobulin.

2. A method according to claim 1 in which the polyvalent intact immunoglobulin is obtained from blood serum fractions by modified alcohol cryoprecipitation including mild acidification at pH 4.

3. A method according to claim 1 in which the dosage administered is from 0.05 to 0.3 g/kg body weight.

4. A method according to claim 3 in which the dosage is 12-18 g repeated at intervals of 2-4 weeks.

5. A method according to claim 1 in which the inflammatory disease is ulcerative colitis.

6. A method according to claim 1 in which the inflammatory disease is Crohn's disease.

* * * * *